United States Patent [19]
Deason et al.

[11] Patent Number: 4,995,260
[45] Date of Patent: Feb. 26, 1991

[54] NONDESTRUCTIVE MATERIAL CHARACTERIZATION

[75] Inventors: Vance A. Deason; John A. Johnson; Kenneth L. Telschow, all of Idaho Falls, Id.

[73] Assignee: The United States of America as represented by the United States Department of Energy, Washington, D.C.

[21] Appl. No.: 379,832

[22] Filed: Jul. 14, 1989

[51] Int. Cl.$^5$ .................................... G01N 29/00
[52] U.S. Cl. .................................... 73/632
[58] Field of Search .............. 73/643, 653, 655, 627, 73/632, 642, 644

[56] References Cited

U.S. PATENT DOCUMENTS 4,567,769 2/1986 Barkhoudarian .................... 73/655

OTHER PUBLICATIONS

"Generation of Elastic Waves by Transient Surface Heating", by R. M. White, Journal of Applied Physics, vol. 34, No. 12, Dec. 1963.
"Laser Excitation of Microwave Sound in Solids", by G. Cachier The Journal of the Acoust. Soc. of America vol. 49, No. 3.

Primary Examiner—Hezron E. Williams
Assistant Examiner—Louis M. Arana
Attorney, Agent, or Firm—Bradley W. Smith; John M. Albrecht; William R. Moser

[57] ABSTRACT

A method and apparatus for nondestructive material characterization, such as identification of material flaws or defects, material thickness or uniformity and material properties such as acoustic velocity. The apparatus comprises a pulsed laser used to excite a piezoelectric (PZ) transducer, which sends acoustic waves through an acoustic coupling medium to the test material. The acoustic wave is absorbed and thereafter reflected by the test material, whereupon it impinges on the PZ transducer. The PZ transducer converts the acoustic wave to electrical impulses, which are conveyed to a monitor.

20 Claims, 6 Drawing Sheets

NONDESTRUCTIVE MATERIAL CHARACTERIZATION

CONTRACTUAL ORIGIN OF THE INVENTION

The United States Government has rights in this invention pursuant to Contract No. DE-AC07-76ID01570 between the United States Department of Energy and EG&G Idaho, Inc.

BACKGROUND OF THE INVENTION

This invention relates to the use of a pulsed laser to excite a piezoelectric transducer as a method of nondestructive characterization of test materials. Conventional ultrasonic piezoelectric (PZ) transducers are excited to emit stress waves by sending a large, short, electrical potential across the piezoelectric transducer. Through the piezoelectric effect, this potential causes stresses in the transducer which are then transmitted out of the PZ transducer into another material in which, in one embodiment, ultrasonic stress waves are induced. In conventional technology, the large electrical signal required to generate the ultrasonic waves causes several problems in the design and construction of the PZ transducer and associated electronics, including limited dynamic range, poor control of the signal shape, and a poor resolution of echoes which return to the PZ transducer a short time after the pulse. PZ transducers have been used in the prior art to generate ultrasonic waves for a microscope having a plurality of imaging modes permitting a two-dimensional scanning of a test sample. In U.S. Pat. No. 4,510,810, issued Apr. 16, 1985, a PZ transducer both transmits and receives ultrasonic waves induced by an RF electric pulse signal.

U.S. Pat. No. 4,641,529, issued Feb. 10, 1987, discloses a pipeline inspection apparatus for detection of corrosion pit defects which avoids the necessity of a liquid or solid-contact coupling. A single PZ transducer transmits and receives ultrasonic energy generated by an electrical RF pulse.

Lastly, U.S. Pat. No. 4,513,384, issued Apr. 23, 1985, discloses the use of a laser and PZ transducer for nondestructively determining the thickness of and defects within thin films deposited on a substrate. Measurement and depth profile determinations are made using a thermal wave detection system.

SUMMARY OF THE INVENTION

Nondestructive material characterization is used to identify a number of material properties, such as the thickness or structural uniformity of the material, location of flaws or defects, and measurement of acoustic velocity. Traditionally, such measurements have been made by inducing stress waves in the test material. This invention replaces the induction of stress waves by an electrical signal induced by a laser pulse. A laser or other light emitting source having a short pulse duration can be mounted directly on or adjacent a PZ material (or otherwise coupled by fiber optics to the PZ material), and can be activated to start the PZ transducer action. After generating the pulsed light beam onto or within the PZ transducer, vibration of the PZ transducer causes an ultrasonic wave to be generated. After being reflected, a PZ transducer receives the returning acoustic wave echoes in the usual manner, by the PZ effect, converting the acoustic waves into electrical signals. The primary advantage of the method and apparatus of the present invention is that the receiving electronics do not have to be electrically isolated from the initiating pulse since the usual large electrical potentials are not present. In prior art apparatus', wherein the same transducer is used to both send and receive the ultrasonic wave, the large voltages (on the order of several hundred volts) required to induce the desired level of transducer excitation requires that the receiving unit be protected from these large energy pulses. Therefore, the electrically noisy input diodes commonly used to reduce the pulse to acceptable levels in the receiving amplifier can be eliminated. Thus, the dynamic range of the receiving amplifier can be increased.

Modeling calculations and experiments performed using the apparatus of the present invention indicate that a laser source is efficient as an exciter for the PZ transducer and can offer significant bandwidth increase, thereby offering increased characterization of the test material. At present, the PZ transducer is the most sensitive detector available and therefore is still preferred for measuring ultrasonic scattering from test material microstructural features.

DETAILED DESCRIPTION OF THE INVENTION

Figure 1:
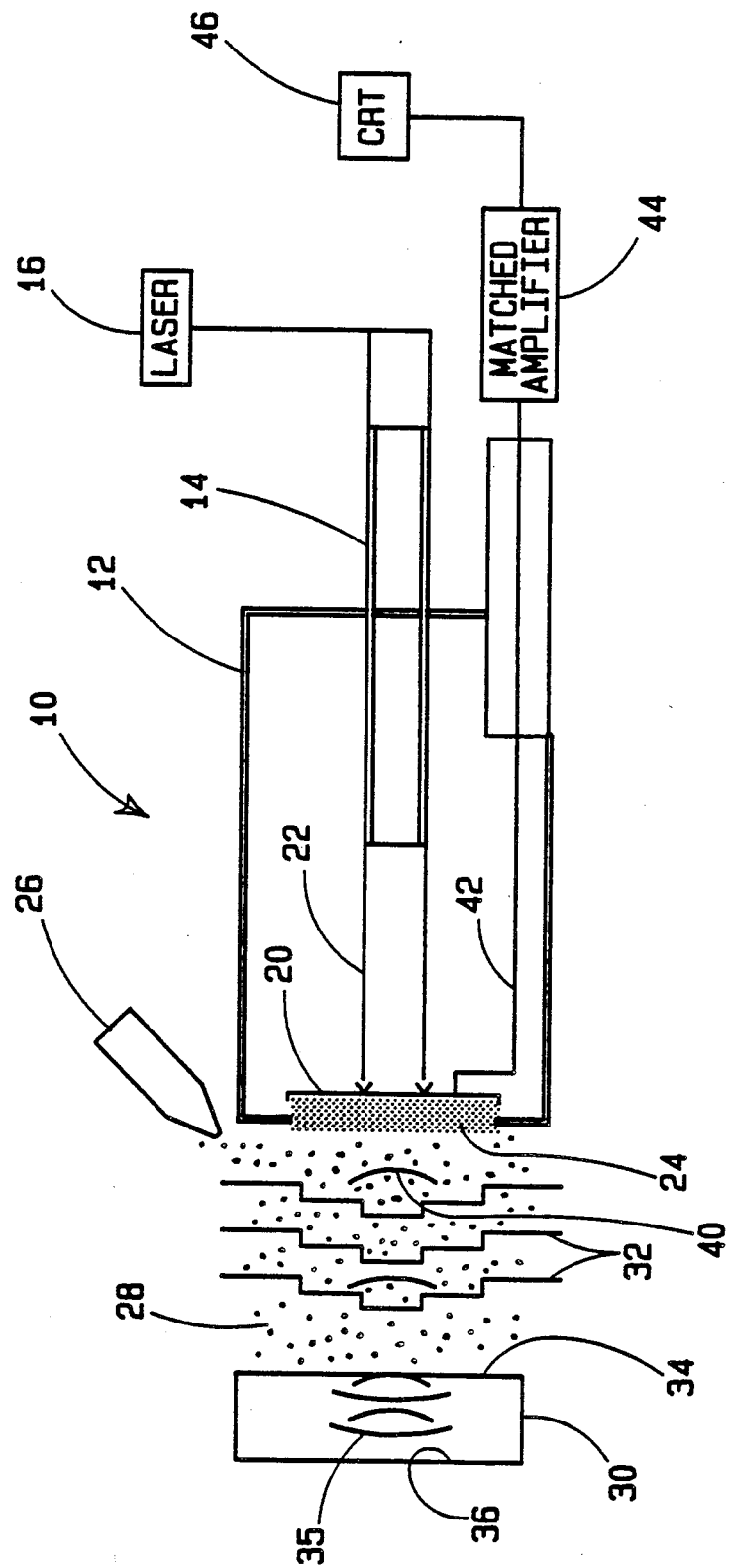
FIG. 1 is a schematic drawing of a first embodiment of the apparatus of the present invention.

Referring to FIG. 1, the apparatus 10 of the present invention, comprising a combination PZ transducer and laser source, is contained within an enclosure 12 through which is directed a fiber optic cable 14. While the device of FIG. 1 is illustrated provided with a fiber optic pulsing system, it is to be understood that any conventional laser pulsing technique may be utilized in the method and apparatus of this invention. The fiber optic cable 14 transmits the laser pulse from a conventional laser 16 to the acoustic backing material 20. Such backing material is preferably optically transparent when used in this embodiment and is formed of epoxy, glass and similar crystalline materials or suitable liquids. This material provides a damping function to reduce the "ringing" in the PZ transducer when the transducer is excited by the laser pulse. The laser-induced optic pulse (indicated by arrow 22) is permitted to pass through the backing material 20 and thereafter strikes the PZ transducer 24. The optical energy of the pulse 22 is absorbed at the interface between the PZ transducer 24 and the backing material 20, and an elastic wave is propagated from this point due to thermoelastic expansion. The PZ transducer disclosed herein is of conventional design. In a preferred embodiment the PZ transducer may be any contact or immersion transducer modified to include a suitable transparent backing material. Conventionally, such transducers are made of, inter alia. quartz, lithium niobate, lead zirconate, titanate, or other well-known materials.

Acoustic coupling medium 28 conducts the acoustic pulse 32 generated by the PZ transducer 24 at the interface to the test material 30. The ultrasonic pulse may be referred to hereinafter as an "acoustic" pulse as it travels through the acoustic coupling medium 28.

As used herein, the coupling medium is preferably water or a glycerin gel or commercially available couplants. Therefore, in a preferred embodiment, a water jet 26 sprays a layer, or film, of water 28 (the acoustic coupling medium) between the transducer 24 and the test material 30 to be tested in a manner well known to those skilled in this technology.

The acoustic pulse 32 strikes a front surface 34 of the test material 30 and is propagated through the material 30 as an ultrasonic wave 35. Depending upon the test purposes, this ultrasonic wave reflects back to the PZ transducer 24 either from the back or far surface 36 of the test material 30 or a flaw, and returns as a reflected acoustic pulse 40. This pulse may be reflected from the front surface 34 of test material 30 and is transmitted through the acoustic coupling medium 28 to the PZ transducer 24, which converts the reflected pulse 40 to an electric signal. This signal is conducted by signal cable 42 to an impedance matched amplifier 44. Any conventional read-out device may be employed to translate the amplifier output for observation. For instance, a cathode ray tube 46 may display the results of the testing of test material 30.

Figure 2:
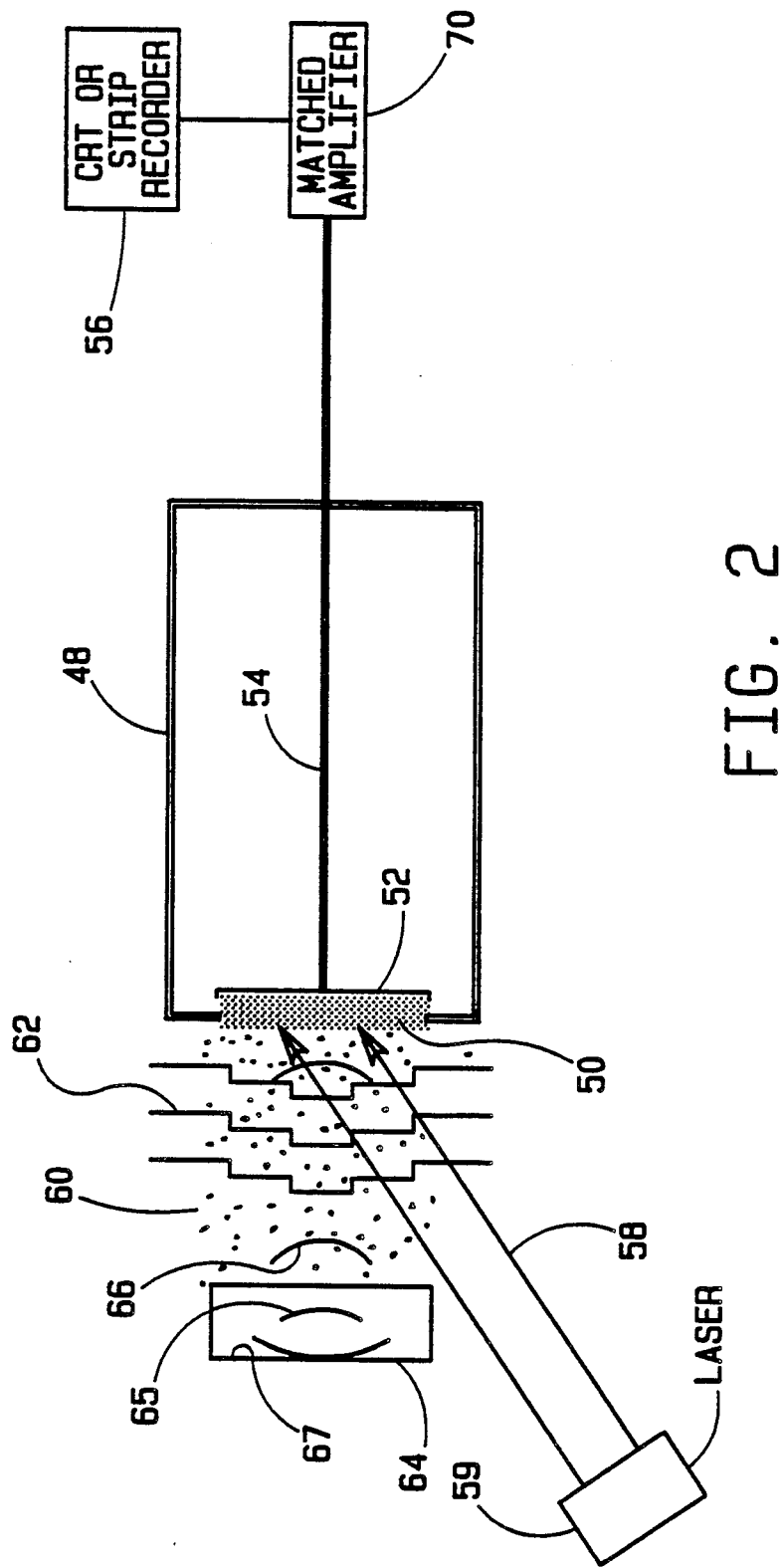
FIG. 2 is a schematic drawing of a second embodiment of the apparatus of the present invention.

In a second embodiment illustrated in FIG. 2, an enclosure 48 is provided with a PZ transducer 50 of conventional design as set forth above. The transducer 50 may be backed by an acoustic (damping) backing material 52. An electrical conductor 54 in the form of a cable conducts the electric signal from the PZ transducer 50 to an impedance-matched amplifier 70 and thence to means 56 to monitor the test result signal, such as a cathode ray tube or strip chart recorder. As opposed to the embodiment of FIG. 1, wherein the laser pulse is induced from behind the transducer, in the embodiment of FIG. 2 the laser 59 is uncoupled from the transducer 50 and a pulse is remotely generated from in front of the transducer 50, rather than from behind as in FIG. 1. The laser pulse 58 is directed through the acoustic coupling medium 60 and strikes the front surface of transducer 50. The transducer 50 then induces an acoustic pulse 62 which travels through the acoustic coupling medium 60, to the test material 64. An ultrasonic wave 65 is propagated through the test material as in FIG. 1, and is reflected back from either the back surface 67 of test material 64, or a flaw. The reflected acoustic pulse 66 is received by the transducer 50 and is conventionally converted into an electrical pulse.

Figure 3A:
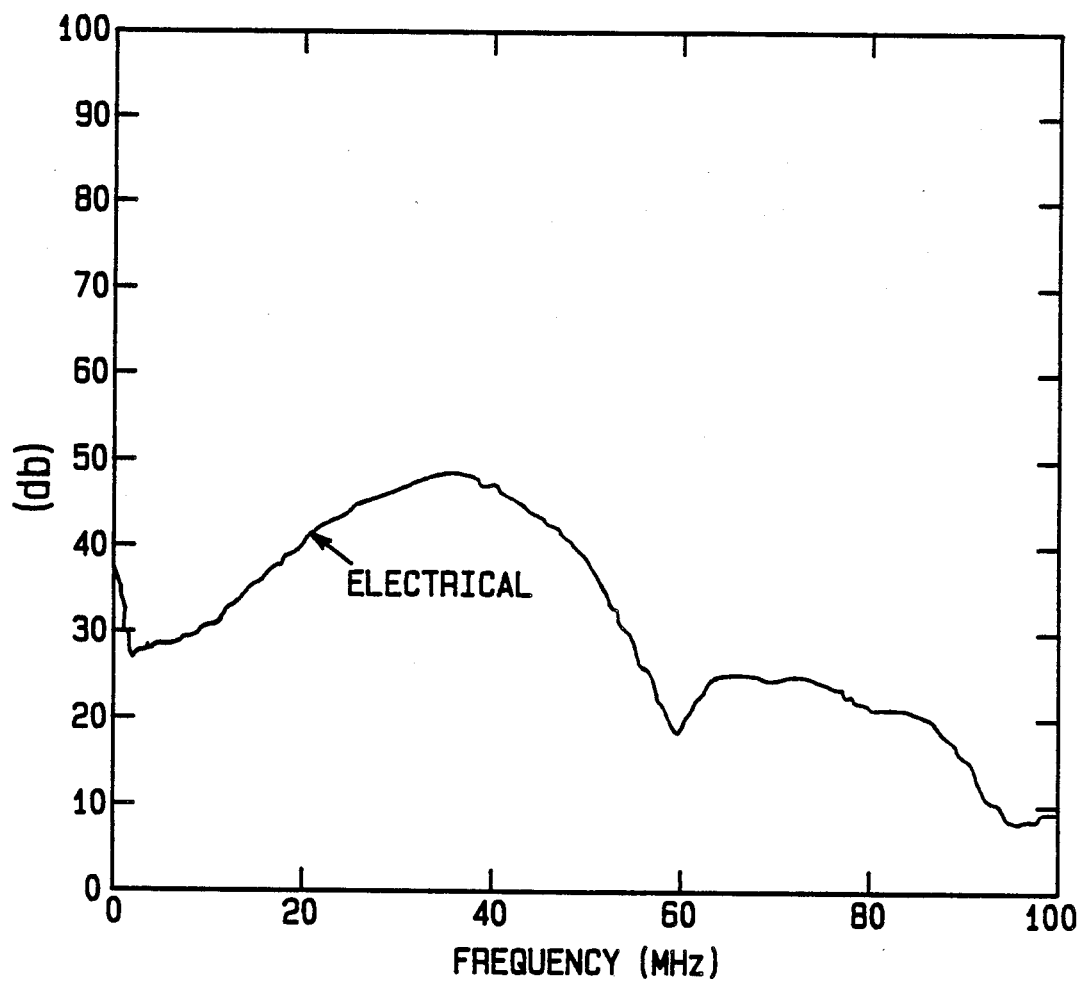
FIG. 3A is a frequency spectra of the waveform detected by a 30 MHz PZ transducer of the prior art with an indication of the usable range.
Figure 3B:
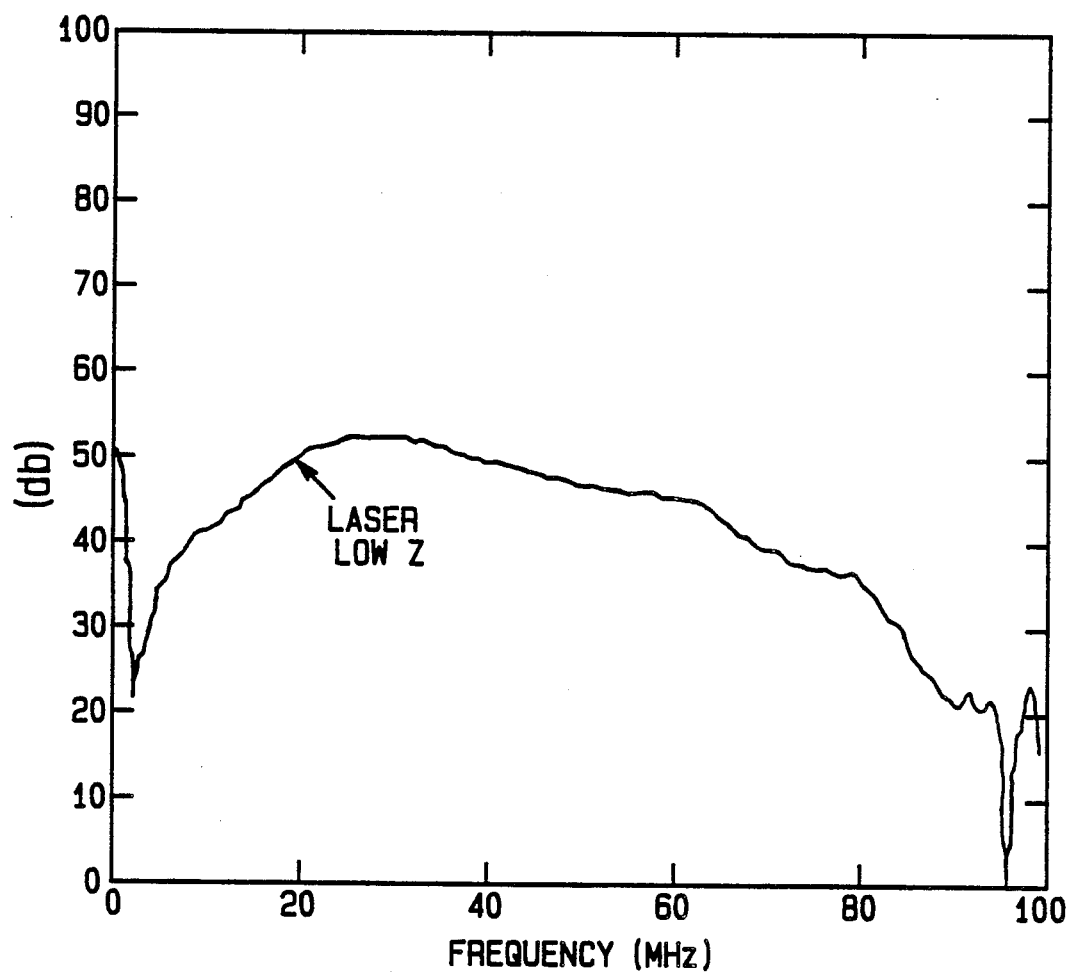
FIG. 3B is a frequency spectra of the waveform detected by a 30 MHz PZ transducer of the present invention with an indication of the usable range.

Experimental and theoretical results have shown the pulsed laser to be a very efficient source of ultrasonic waves by both excitation of PZ transducers and direct generation through thermoelastic expansion of the material surface. Large ultrasonic amplitudes and wide bandwidths have been recorded with the laser source, bringing improvements in microstructural characterization through increased signal to noise ratios and decreased flaw size resolution. Using the laser as a source separates the source electrical circuit from the detection electrical circuit in contrast to the conventional electrical excitation technique which requires that both source and detector electronics be connected. A direct consequence of this decoupling is that the receiving electronics can be better matched to the PZ transducer, which results in improved frequency response for the transducer/amplifier combination. This enhancement of the frequency response is shown in FIG. 3 where frequency spectra using electrical excitation (FIG. 3A) as previously practiced are compared with the laser excitation (FIG. 3B) of the present invention for a given input impedance (Z) amplifier. Higher frequency measurements are desired for microstructure characterization of test materials as increased ultrasonic scattering takes place from small defects. This results in increased sensitivity to small microstructure features which are on the order of the ultrasonic wave length in size. The pulsed laser provides a much broader useful frequency range over which these characterizations can be made.

Laser excitation experiments were conducted using a pulsed laser to excite PZ transducers at from 5–85 MHz. In all cases, the actual detected waveform had a frequency spectrum essentially identical to that of the PZ transducer used. This indicates that the actual excitation waveform produced was of very short rise time, corresponding to the laser pulse of about 5 nanoseconds. In one experimental arrangement the transducer was bonded to a glass plate through which the laser pulse was directed. The optical energy was absorbed at the PZ transducer/glass interface and the acoustic wave propagated from this point was reflected from the outer glass surface. The acoustic wave subsequently returned to the transducer/glass interface and was detected by the PZ transducer. This arrangement allowed both the excitation mechanism and propagation of the elastic wave to be recorded in one experiment.

Figure 4A:
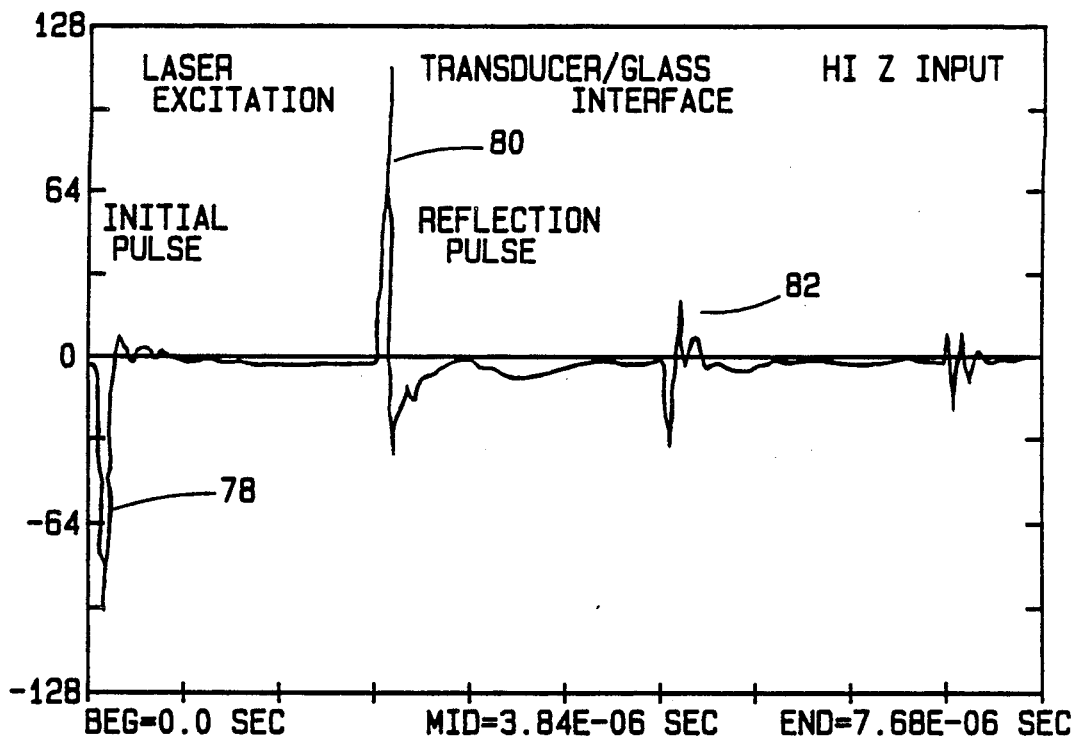
FIG. 4A is an actual waveform of the present invention; using a high impedance amplifier.
Figure 4B:
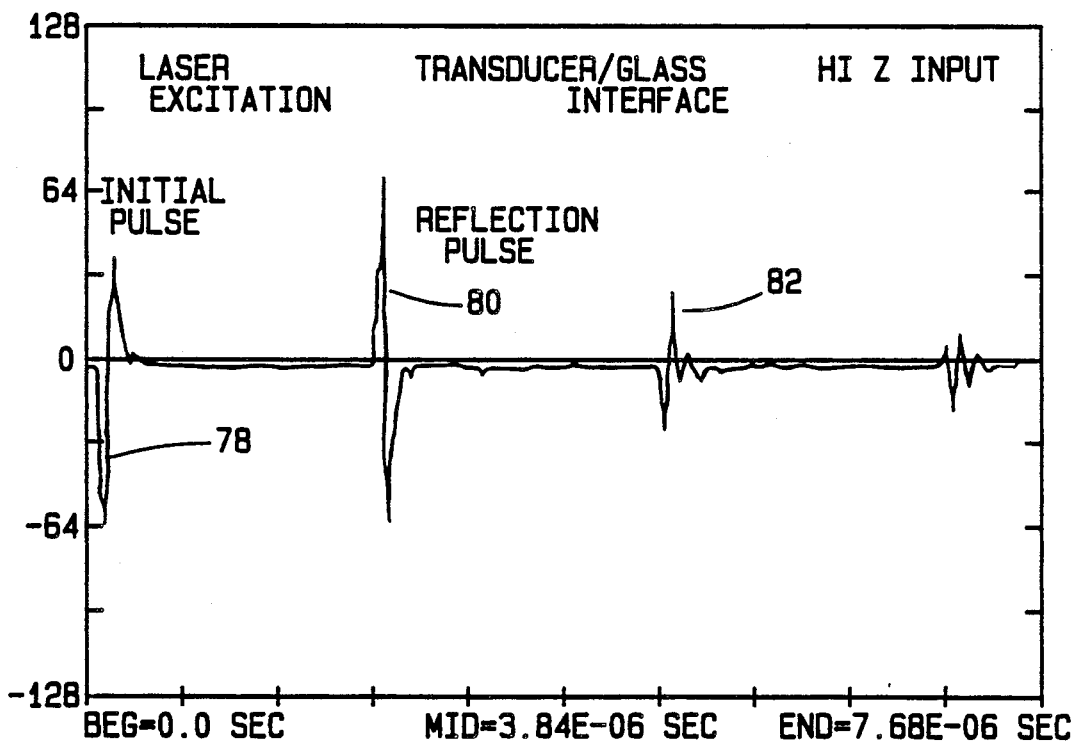
FIG. 4B is an actual waveform using a low impedance amplifier of the present invention.

FIG. 4A illustrates the detected signals obtained from a 5 MHz contact longitudinal transducer bonded to a 0.25 inch thick glass plate and pulsed as illustrated in FIG. 2. The signals were amplified by a high input impedance amplifier, yielding a voltage output proportional to the difference in excitation of the two surfaces of the transducer. The results of FIGS. 4A and 4B illustrate the longitudinal displacement waves 78 generated when the laser pulse is absorbed over the entire surface of the transducer (an indication of the thermoelastic expansion, a direct measure of the absorbed optical energy) and subsequent reflections (80, 82) of the propagated wave between the faces of the transducer and the outer glass surface. The only difference between the two FIGURES is that the results of FIG. 4A reflect a high impedance amplifier and FIG. 4B reflects a low impedance amplifier. With a high impedance amplifier, the waveforms correspond to the net displacement between the two transducer faces. With a low impedance amplifier, the detected waveforms correspond to the net velocity difference between the transducer faces. The waveform of FIG. 4B is essentially the derivative of that in FIG. 4A. The magnitude of the waveforms show the generation process to be efficient and subsequent measurements indicate it to be linear up to power densities which ablate the metallic absorbing film on the surface of the transducer.

The advantage of the process disclosed above is that the source and receiver electrical circuits can be separated from one another, thereby eliminating the need to apply the high voltage excitation pulse to the receiver input, thereby avoiding any overload. Additionally, the receiving electronics can be better matched to the transducer, resulting in improved frequency response for the transducer/amplifier combination.

Figure 5:
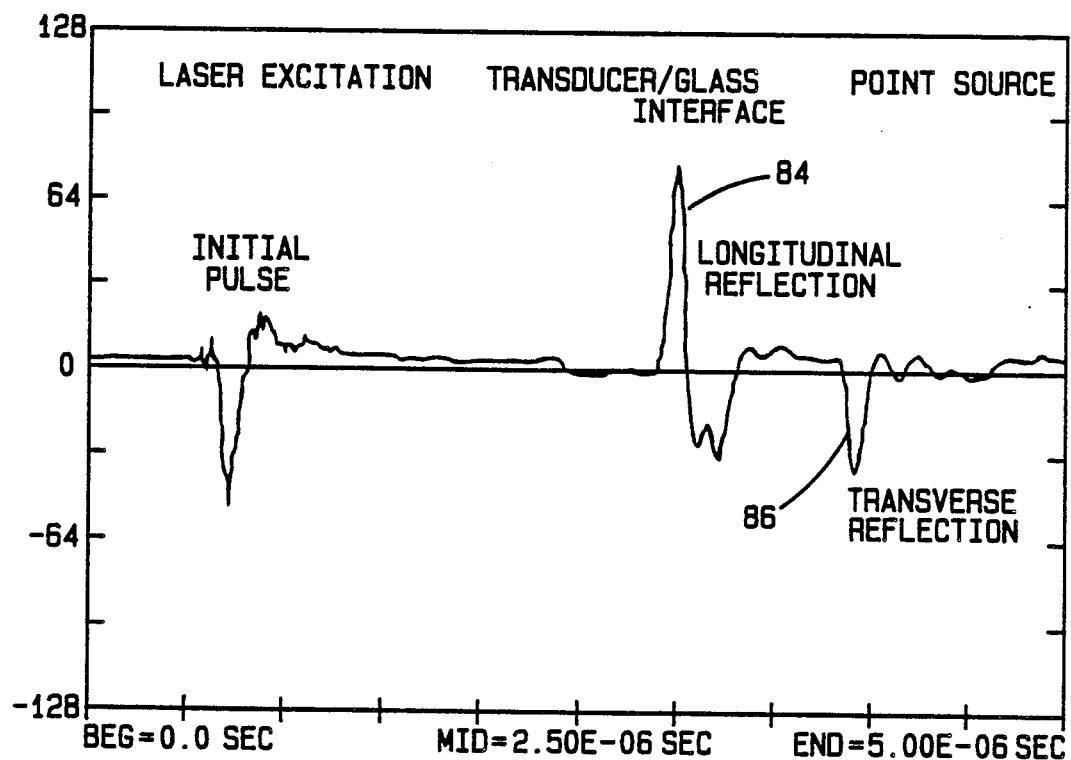
FIG. 5 is a waveform resulting from laser excitation through 1 mm aperture.

A further test was made using a laser beam focused to a small spot size of approximately 1 mm diameter, in order to test its ability to excite transverse modes of the primarily longitudinal mode transducer. As illustrated in FIG. 5, in addition to the longitudinal waveform 84, a later wave 86 is observed, which is a transverse wave. The thermoelastic expansion mechanism produces both longitudinal and transverse expansions, even with the stressed boundary condition used in this experiment. The efficiency of transverse wave generation can be greatly increased when the PZ transducer surface (where the laser pulse is absorbed) is free of stress. The ability of the laser source to simultaneously generate longitudinal and transverse waves can be useful for rapid ultrasonic velocity determination in cases where anisotropy or elastic constants are to be measured.

Figure 6A:
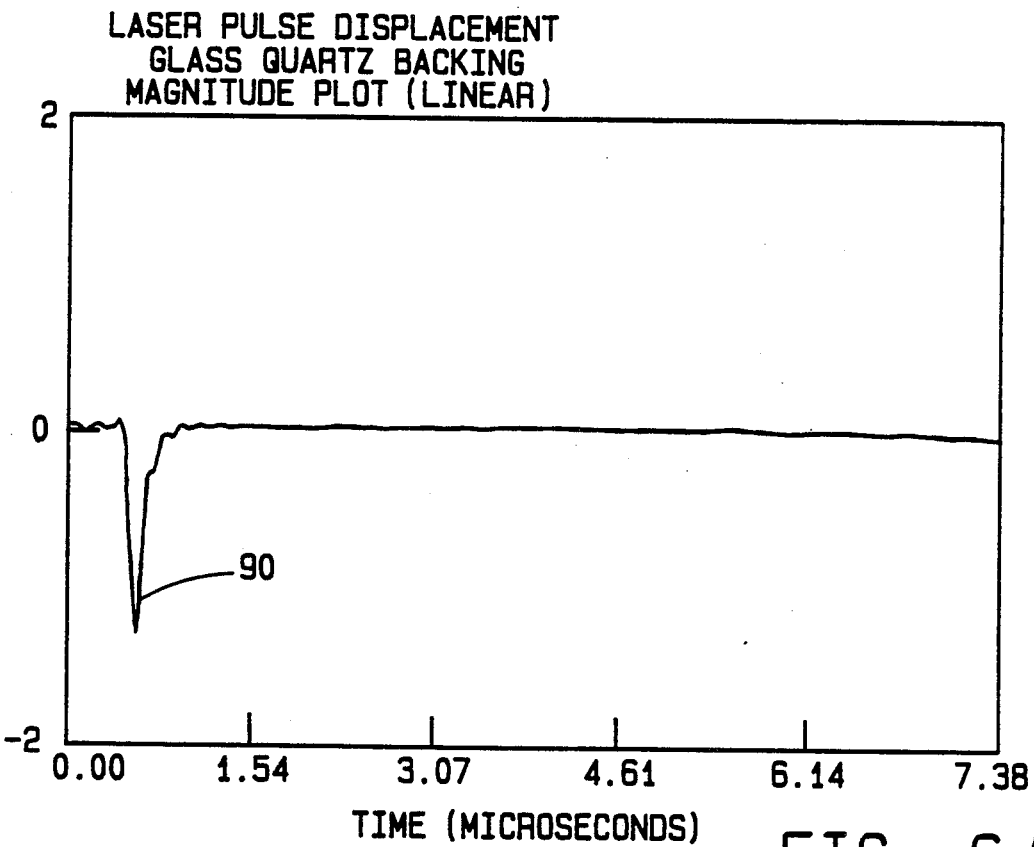
FIG. 6A is a calculated waveform from the embodiment illustrated in FIG. 2.
Figure 6B:
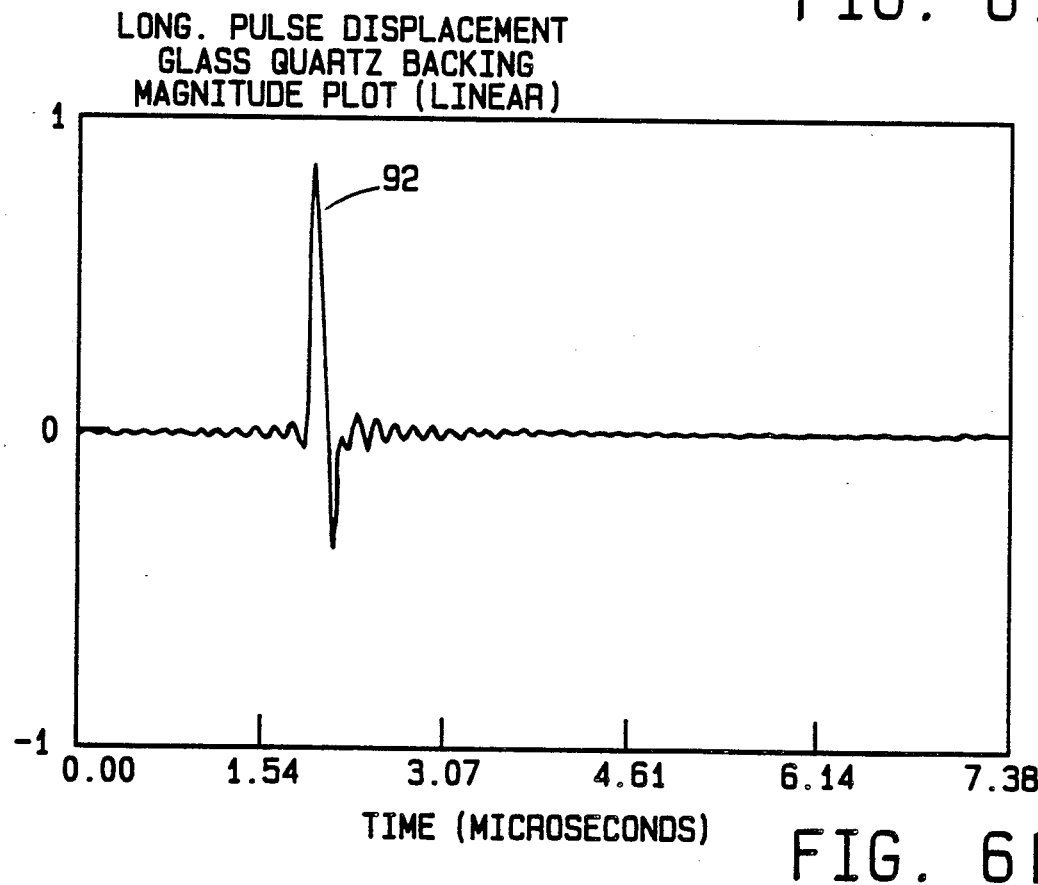
FIG. 6B is a calculated first longitudinal reflected waveform from the embodiment of FIG. 2.

A mathematical model was developed to simulate the excitation of PZ transducers using pulsed laser light. The radiation pulse is assumed to be of high energy and of very short duration and is absorbed within a very short distance from the surface. This represents an impulse of heat into the transducer which causes local volumetric expansion and excitation of longitudinal, transverse and surface waves. These waves excite modes of vibration in the disk-shaped transducer, which rings near its resonant frequency. The model is based on a Mason equivalent circuit for the resonant transducer with the light pulse treated as a current source. Resultant longitudinal waves launched into an adjacent specimen can be calculated for excitation on either side of the transducer. Backing material and specimen properties, along with the transducer properties, are taken into account. Calculations from this model are very useful for designing excitation experiments with both commercial and fabricated transducers and mounting assemblies. FIGS. 6A and 6B illustrate the calculated waveform (90 of FIG. 6A) to be analogous to wave 78 of FIG. 4A, and the calculated first longitudinal reflected waveform (92 of FIG. 6B) to be analogous to the reflection wave 80 of FIG. 4A. Most of the essential features of the experimentally measured waveforms are duplicated in the model, which confirms the basic understanding of the process.

One important aspect of the pulse generation process of the present invention is that the pulse source and pulse receiver can be totally separated. The advantage over conventional electrical excitation is that the high voltage excitation pulse need not be applied to the receiver input and therefore no overload will occur. The net result is that the actual generation process itself can be detected (as shown in FIG. 3), and electrical coupling of the transducer to the amplifier can be matched without regard to the source electrical characteristics.

The use of these laser methods in conjunction with the comparison of test materials with known or calibrated materials will allow rapid and efficient characterization of materials or identification of material structural defects. While preferred embodiments of the invention are disclosed, various modes of carrying out the principles disclosed herein are contemplated as being within the scope of the following claims. Therefore, it is understood that the scope of the invention is not to be limited except as otherwise set forth in the claims.

We claim:

1. A method for nondestructive material characterization comprising:
   acoustically coupling a piezoelectric (PZ) transducer to test a material;
   exciting the PZ transducer using a pulsed laser such that the transducer generates an acoustic pulse which impacts the test material;
   propagating an ultrasonic wave generated from said acoustic pulse through at least a portion of the test material;
   reflecting said ultrasonic wave from the test material back to the transducer as a reflected acoustic pulse;
   generating an electrical signal from the interaction of said reflected acoustic pulse and said PZ transducer and inputting said electric signal to an impedance matched amplifier to produce an amplified signal; and
   coupling said amplifier to a read-out device to measure the amplified signal.

2. The method as recited in claim 1, further comprising the step of acoustically coupling the PZ transducer to the test material with a material selected from the group consisting essentially of water, glycerin, and acoustic couplants, or combinations thereof.

3. The method as recited in claim 1, wherein the PZ transducer is made of a material selected from the group consisting essentially of quartz, lithium, niobate, lead zirconate, titanate, or combinations thereof.

4. The method as recited in claim 3, further comprising securing the PZ transducer to an optically transparent backing material.

5. The method as recited in claim 4, further comprising positioning the transparent backing material between the pulsed laser and the PZ transducer.

6. The method as recited in claim 4, further comprising positioning the PZ transducer between the pulsed laser and the transparent backing material.

7. The method as recited in claim 1, further comprising coupling the pulsed laser to the PZ transducer by a fiber optic cable.

8. The method as recited in claim 1, wherein the PZ transducer is provided with a front surface and a rear surface, and directing the laser pulse at the rear surface, such that the acoustic wave is propagated from the front surface of the PZ transducer.

9. The method as recited in claim 8, wherein the reflected acoustic wave is received by the front surface of the PZ transducer and converted to electrical impulses for transmission to a recording device.

10. The method as recited in claim 1, wherein the PZ transducer is provided with a front surface and a rear surface, and directing the laser pulse at the front surface, such that the acoustic wave is propagated from the front surface of the PZ transducer.

11. Apparatus for nondestructive material characterization, comprising:
   a. a pulsed laser;
   b. a piezoelectric (PZ) transducer optically coupled to said pulsed laser for receiving a light pulse from said pulsed laser;
   c. an acoustic backing material affixed to a rearward side of the PZ transducer;
   d. an electrical conductor interconnected with the PZ transducer to conduct an electrical signal from the PZ transducer to a recording device.

12. The apparatus of claim 11, wherein said apparatus further comprises means to acoustically couple the PZ transducer to said material.

13. The apparatus of claim 12, wherein said means to acoustically couple the PZ transducer to said material comprises a water jet to apply a water film between the material and the PZ transducer.

14. The apparatus of claim 11, wherein fiber optic means are provided to conduct a laser pulse from the pulsed laser to the PZ transducer.

15. The apparatus of claim 14, wherein the acoustic backing material is disposed between the PZ transducer and the pulsed laser.

16. The apparatus of claim 11, wherein the PZ transducer is disposed between the pulsed laser and the acoustic backing material.

17. Method for improved frequency response of a PZ transducer, comprising:
 a. bonding a surface of a PZ transducer to an optically transparent acoustic backing material;
 b. directing a beam from a pulsed laser onto the PZ transducer;
 c. generating an elastic pulse at said bonding surface of said PZ transducer;
 d. reflecting the elastic pulse from a test material; and
 e. receiving the reflected elastic pulse at the PZ transducer, an converting the received elastic pulse to an electric signal for display.

18. The method as recited in claim 17, further comprising directing the laser pulse through the optically transparent acoustic backing material and thence through the PZ transducer.

19. The method as recited in claim 17, further comprising directing the laser pulse through the PZ transducer and thence through the optically transparent acoustic backing material.

20. The method as recited in claim 17, further comprising converting the received elastic pulse to an electric signal with a low input impedance amplifier.

* * * * *